United States Patent [19]

Banholzer

[11] Patent Number: 4,755,603

[45] Date of Patent: Jul. 5, 1988

[54] PROCESS FOR THE PREPARATION OF NORSCOPINE

[75] Inventor: Rolf Banholzer, Ingelheim am Rhein, Fed. Rep. of Germany

[73] Assignee: Boehringer Ingelheim KG, Ingelheim am Rhein, Fed. Rep. of Germany

[21] Appl. No.: 53,956

[22] Filed: May 26, 1987

Related U.S. Application Data

[63] Continuation-in-part of Ser. No. 906,550, Sep. 12, 1986, abandoned, which is a continuation of Ser. No. 626,693, Jul. 2, 1984, abandoned, which is a continuation-in-part of Ser. No. 485,187, Apr. 15, 1983, abandoned.

[30] Foreign Application Priority Data

Apr. 26, 1982 [DE] Fed. Rep. of Germany ....... 3215490

[51] Int. Cl.$^4$ ............................................. C07D 491/08
[52] U.S. Cl. ...................................................... 546/91
[58] Field of Search ......................................... 546/91

[56] References Cited

U.S. PATENT DOCUMENTS 4,608,377 8/1986 Banholzer ........................... 514/291

Primary Examiner—Alan L. Rotman
Attorney, Agent, or Firm—Weissenberger, Hammond & Littell

[57] ABSTRACT

Norscopine is prepared from norscopolamine by hydrogenation cleavage with a complex hydride in an inert solvent at room temperature.

2 Claims, No Drawings

PROCESS FOR THE PREPARATION OF NORSCOPINE

This is a continuation-in-part of copending application Ser. No. 06/906,550, filed Sept. 12, 1986, now abandoned which in turn is a continuation of application Ser. No. 06/626,693, filed July 2, 1984, now abandoned; which in turn is a continuation-in-part of application Ser. No. 06/485,187, filed Apr. 15, 1983, now abandoned.

This invention relates to a novel process for the preparation of norscopine.

THE PRIOR ART

Norscopine is mentioned in an article by Long-Nan Chao entitled "A rapid method for the detection of some drugs mixed in Chinese herb preparation by thin-layer chromatography" [T'ai-wan K'o Hsueh 1980, 34 (3-4), 181–185; abstracted in C.A. 94, 1981, pg. 153, No. 59168e; the Tenth Collective Index, pg. 35768 CS, Columbus, Ohio] as an illicit constituent of herb medicine preparations.

Moreover, norscopine is embraced by the generic claim of German Auslegeschrift No. 1,670,257.

*The Alkaloids* by R. H. F. Manske et al., Vol. 1 (1950), page 307; Academic Press, Inc., New York, N.Y.; and *The Plant Alkaloids* by T. A. Henry, 3rd Ed. (1939), page 93; Churchill Ltd., London, England, describe the partial conversion of scopolamine—in addition to the formation of its N-oxide—into scopinium bromide, followed by conversion of the latter into pseudoscopine with sodium amalgam.

The application of this process to norscopolamine, however, would not make sense because the formation of pseudonorscopine is not desired.

DESCRIPTION OF THE INVENTION

More particularly, the present invention relates to a process for the preparation of norscopine, which comprises treating norscopolamine or a salt thereof with a complex metal hydride, preferably at room temperature or at lower temperatures, in an inert solvent. Metal borohydrides, preferably sodium borohydride (NaBH$_4$), are particularly suitable. Lithium alanate is also theoretically suitable; however, temperatures of 0° C. and below should then be used to avoid secondary reactions.

A particularly suitable solvent for the reaction described above is ethanol. Higher alcohols and other organic solvents, such as ether, are less favorable since norscopolamine salts, which are preferably used as starting compounds, do not readily dissolve therein. Methanol is not particularly suitable either since it decomposes sodium borohydride, for example, very rapidly, even at 0° C., thereby requiring the use of an unnecessarily large quantity of this reagent. The hydrogenolysis may also be effected in water if, for example, the pH is adjusted to about 6 to 7. However, it is more difficult to isolate the norscopine afterwards from water than from ethanol.

The preparation of norscopolamine is described in German Auslegeschriften Nos. 1,670,257 and 1,670,258.

Norscopine may also be obtained in the form of acid addition salts after reaction with inorganic or organic acids. Suitable acids include, for example, hydrochloric, hydrobromic, sulfuric, phosphoric, tartaric, fumaric, citric, maleic, succinic, gluconic, malic, p-toluenesulfonic, methanesulfonic, and amidosulfonic acid.

The following example illustrates the present invention and will enable others skilled in the art to understand it more completely. It should be understood, hwoever, that the invention is not limited solely to the particular example given below.

EXAMPLE 1

Norscopine and its hydrochloride 32.6 gm (0.1 mol) of norscopolamine hydrochloride was suspended in 350 ml of ethanol, and the resulting suspension was combined with a total of 3.78 gm (0.1 mol) of sodium borohydride in six portions at intervals of 20 minutes, while constantly stirring, at a temperature of 20° C. The resulting mixture was allowed to react for 12 hours, at the end of which hydrogenolysis was complete. Then, at from −5° to −10° C., hydrogen chloride gas was introduced into the reaction mixture in an atmosphere of nitrogen until an acid reaction was obtained. The solution was washed with 1.5 liters of ether to remove the hydrogen chloride. After drying, the crystals which separated out were finely triturated and suspended in 2 liters of methylene chloride, and the suspension was then heated to boiling. Subsequently, ammonia was introduced into the boiling methylene chloride to form the base, until completion of the reaction. After the inorganic salts were separated, the methylene chloride was distilled off under reduced pressure at 30° C.

Norscopine crystallized out in the form of colorless crystals.

M.p.: 198°–202° C. (decomposition),

Yield: 12.0 gm (85.7% of theory).

The hydrochloride was prepared by conventional methods. Colorless crystals (ethanol), melting point: 292°–293° C. (decomposition), conversion point: ~205° C.

The presence of this compound was confirmed by elemental analysis and spectra.

Norscopine of the formula

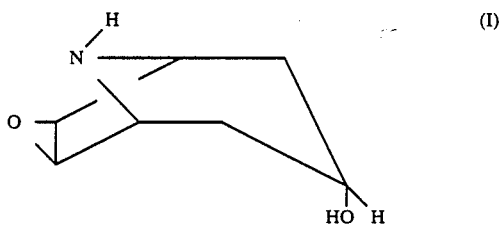

and the acid addition salts thereof constitute valuable products which are useful, for example, in the preparation of 6,11-dihydro-dibenzo-[b,e]-thiepine-11-N-alkyl-norscopine ethers of the formula

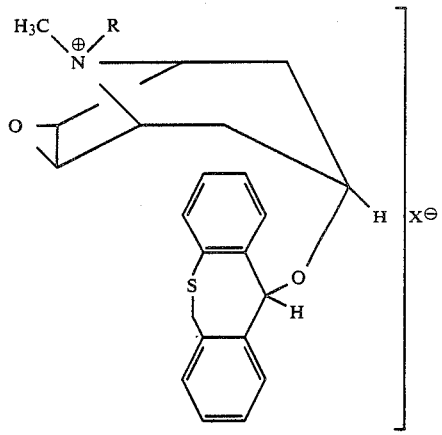

(II)

wherein R is linear or branched alkyl of 1 to 10 carbon atoms, and $X^{\ominus}$ is a non-toxic, pharmacologically acceptable anion such as a halogen or an organic sulfonic acid group. These compounds of the formula II are pharmaceuticals with a well-balanced ratio of anticholinergic and antihistaminic activities, and are therefore particularly suitable for use as bronchospasmolytics. These compounds and their preparation are described in U.S. Pat. No. 4,608,377.

Norscopine can be converted into an ester such as norscopolamine by acylation or transesterification, as disclosed in U.S. Pat. No. 3,583,996.

While the present invention has been illustrated with the aid of a certain specific embodiment thereof, it will be readily apparent to others skilled in the art that the invention is not limited to this particular embodiment, and that various changes and modifications may be made without departing from the spirit of the invention or the scope of the appended claims.

I claim:

1. The method of preparing norscopine or an acid addition salt thereof, which comprises subjecting norscopolamine or an acid addition salt thereof to hydrogenation cleavage with sodium borohydride in ethanol.

2. The method of claim 1, wherein said hydrogenation cleavage is performed at room temperature.

* * * * *